United States Patent [19]

Klainer et al.

[11] Patent Number: 4,892,383
[45] Date of Patent: Jan. 9, 1990

[54] RESERVOIR FIBER OPTIC CHEMICAL SENSORS

[75] Inventors: Stanley M. Klainer, San Ramon; Kisholoy Goswami, Walnut Creek, both of Calif.; Nelson R. Herron, Lachini, Mich.; Stephen J. Simon; Lawrence A. Eccles, both of Las Vegas, Nev.

[73] Assignee: FiberChem Inc., Las Vegas, Nev.

[21] Appl. No.: 312,645

[22] Filed: Feb. 17, 1989

[51] Int. Cl.[4] .......................... G02B 6/02; H01J 5/16; A61B 5/00; G01N 21/00

[52] U.S. Cl. .................. 350/96.29; 350/96.18; 350/96.20; 250/227; 250/226; 250/237 R; 250/239; 128/634; 128/636; 356/39; 436/164; 436/165; 436/171; 436/805

[58] Field of Search .............. 350/96.10, 96.15, 96.18, 350/96.20, 96.29, 96.30; 250/227, 226, 237 R, 239; 128/633, 634, 636, 637; 356/39; 436/164, 165, 171, 805

[56] References Cited

U.S. PATENT DOCUMENTS

| | | | |
|---|---|---|---|
| 4,197,852 | 4/1980 | Schindler et al. | 128/635 |
| 4,200,110 | 4/1980 | Peterson et al. | 128/634 |
| 4,344,438 | 8/1982 | Schultz | 128/634 |
| 4,356,396 | 10/1982 | Ruell et al. | 250/227 |
| 4,399,099 | 8/1983 | Buckles | 436/805 X |
| 4,476,870 | 10/1984 | Peterson et al. | 128/634 |
| 4,599,901 | 7/1986 | Hirschfeld | 250/227 X |
| 4,608,344 | 8/1986 | Carter et al. | 436/164 X |
| 4,666,672 | 5/1987 | Miller et al. | 128/632 |
| 4,678,904 | 7/1987 | Saaski et al. | 250/227 |
| 4,682,895 | 7/1987 | Costello | 350/96.29 X |
| 4,737,343 | 4/1988 | Hirschfeld | 128/633 X |
| 4,749,856 | 6/1988 | Walker et al. | 250/227 |
| 4,778,987 | 10/1988 | Saaski et al. | 250/226 |
| 4,782,226 | 11/1988 | Jeffries, Jr. et al. | 250/227 |
| 4,785,814 | 11/1988 | Kane | 128/634 |
| 4,801,187 | 1/1989 | Elbert et al. | 350/96.15 |
| 4,824,206 | 4/1989 | Klainer et al. | 350/96.29 |
| 4,824,789 | 4/1989 | Yafuso et al. | 250/227 X |
| 4,834,496 | 5/1989 | Blyler, Jr. et al. | 350/96.29 |

*Primary Examiner*—John D. Lee
*Assistant Examiner*—Brian M. Healy
*Attorney, Agent, or Firm*—Henry P. Sartorio

[57] ABSTRACT

A reservoir fiber optic chemical sensor (FOCS) is formed of a modular cell body. A fiber optic is attached using a quick connect standard fiber optic connector. A semipermeable membrane is attached at the opposite end of the cell body using a quick attach membrane retainer. Multiple sensors can be made uniformly. Specific sensors for TCE vapor, $O_2$ and $CO_2$ are produced by utilizing a suitable reaction chemistry in the cell. A non-imaging optical focusing element can be included in the cell to increase sensitivity. A reaction cell can be placed adjacent to the reservoir cell with the semipermeable membrane separating the two cells to produce a photolysis FOCS. TOC and TOCl can be detected with the photolysis FOCS.

20 Claims, 4 Drawing Sheets

RESERVOIR FIBER OPTIC CHEMICAL SENSORS

BACKGROUND OF THE INVENTION

The invention relates to fiber optic chemical sensors (FOCS) and more particularly to reservoir FOCS.

The basic FOCS design is a tip coated FOCS in which a reagent that specifically and sensitively interacts with the analyte of interest is placed or attached at the tip of an optical fiber. Fibers in the 100 to 600 micron diameter range are most often used. Unfortunately, because of the very small surface areas at their tips ($7 \times 10^{-5}$ to $3 \times 10^{-3}$ cm$^2$) it is difficult to get enough chemistry at the end of the fiber for reliable measurements, i.e. good signal to noise.

Several approaches have been used to get enough chemistry onto the tip of the fiber and thus overcome the surface area limitations, including: (i) surface amplification techniques, a unique type of covalent immobilization in which the sensing material is attached to the tip by a surface amplification polymer; (ii) imbedding the chemistry into a membrane placed at the tip of the fiber; (iii) large surface area porous glass fibers attached to the tip; and (iv) use of very sensitive chemistry, i.e. fluorescence reactions. In special situations, where the species to be measured is volatile, reservoir FOCS (liquid reagents) with gas permeable membranes have been used. Each of these has shown severe drawbacks. The surface amplification approach works but it is impossible to make several FOCS, either individually or by a batch process, which are similar. Imbedding the chemistry in the membrane results in such disadvantages as slower response times, "leaking" of the reagents and difficulty in making uniform systems. Porous glass fibers, especially the newer ones with the larger pores ($>300$ $\mu$m), appeared to be a big breakthrough, but the large buffering capacity of the glass is a major problem as is its ability to trap unwanted molecules. The use of fluorophores, in the past, has been considered a drawback because of bleaching problems. Finally reservoir cells have been very difficult to use and to make uniformly, and it is also burdensome to obtain reliable data.

Evanescent wave FOCS and side coated FOCS, particularly the multilayered FOCS where the reacting chemistry is sandwiched between the core and clad as described in copending U.S. patent application Ser. No. 046,986, now U.S. Pat. No. 4,846,548, are alternative FOCS designs where the sensing material can be placed on the sides of the fiber.

The need for high resolution, long active lifetimes and good reproducibility between sensors for a particular species indicates the desirability of an improved reservoir sensor. The sensing agents are in liquid form and kept in the sensor by the gas permeable membrane. All of the key elements of the sensor should be very accurately controlled. Ideally, reagent solution can be made with a very high degree of repeatability, the active volume can be precisely controlled, the field-of-view of the fiber is accurately known and the size of the membrane can be held to good tolerance. Thus a design is needed which can incorporate all these features and advantages. The big drawback of the reservoir FOCS is size. It is about 1 cm in diameter compared to other FOCS which are 400 to 600 $\mu$m.

Thus while reservoir FOCS would be particularly desirable for many applications, including sampling in an aqueous environment, present sensors are inadequate.

U.S. Pat. Nos. 4,737,343 to Hirshfeld and 4,666,672 to Miller et al. show typical reservoir FOCS formed by attaching a capillary tube coaxially to the end of an optical fiber using a gas bubble or membrane to close the tube. This structure is difficult to assemble accurately, difficult to control and use and impossible to reproduce uniformly. Another type of FOCS, while not actually a reservoir type, is shown by U.S. Pat. No. 4,476,870 to Peterson et al. wherein a porous polymer jacket or envelope is placed at the end of a pair of fibers and encloses a fluorescent dye on a solid (particulate) support.

The ability to detect or monitor trace amounts of chemical species in situ is of great importance and generally difficult to do. Particular applications include environmental monitoring, pollution control, public health and safety, and industrial monitoring. Groundwater and seawater monitoring are very important. The improved reservoir FOCS would be particularly desireable for many of these applications.

Trichloroethylene (TCE) heads the U.S. Environmental Protection Agency (EPA) list of hazardous (toxic, carcinogenic, etc.) compounds and the organic chlorides, as a group dominate the top ten (10) most frequently found dangerous compounds. Furthermore, total organic carbon is an indicator of the total amount of organic species present. Thus the ability to monitor TCE vapor, total organic chloride (TOCl) and total organic carbon (TOC) are very significant.

TCE is of particular concern because it forms the carcinogen vinyl chloride in water. Moreover, it is estimated that about 23 million people in the United States are exposed each year to TCE levels ranging from 500 ppb to 5 ppm even though $<5$ ppb is considered the safe limit.

Drinking water standards require that these compounds have a concentration of $<5$ ppb if the water is to be considered safe to drink. To assure that the EPA standards are met dictates that drinking water be monitored on a routine basis. To accomplish this task requires that a device be developed that is both inexpensive to purchase and operate and that can give reliable results in the hands of a moderately trained field technician.

The importance of safe and plentiful ground water supplies cannot be overstated. Yet domestic water quality is being threatened in many areas by the intrusion of toxic contaminants into the soil and the ground water from agricultural runoff of pesticides and herbicides; industrial discharge into lakes and rivers; and seepage from solid waste sites (landfills, storage lagoons, and waste piles).

Unlike surface contaminants, which are quickly diluted, chemicals in the soil and ground water often remain highly concentrated both underground and in the water which flows from the faucet. The potential magnitude of the problem is enormous. The EPA has identified thousands of industrial sites containing potentially hazardous wastes which have no safeguards to prevent seepage and there are over 275,000 Subtitle D municipal and industrial sites which may contain dangerous materials. It is, therefore, essential that an economical, practical water monitoring system be in place as soon as possible.

In order to provide adequate protection of water sources, methods of detecting low concentration of toxic contaminants are urgently needed. The public health, as well as the public's confidence in domestic water supplies, requires an early warning system so that prompt action may be taken to track down the sources of the contamination and to take appropriate steps to protect the public. In order to assure soil and water quality first requires that the contaminants be identified. Presently, sophisticated state-of-the-art equipment and methodologies have been used for diagnostic investigation. Wells sometimes must be drilled for proper access to the vadose zone and ground water. Typically gas chromatography, mass and atomic (absorption and emission) spectroscopy have been used in conjunction with special pumps and samplers to collect the soil and water to be analyzed. Unfortunately, present technologies are not highly suitable for continuous and widespread monitoring of groundwater contamination. Problems include the contamination of samples by well construction materials, degradation of sample integrity by most sampling techniques which could result in questionable data and make enforcement difficult, the high capital investment in complex equipment, and the need for highly skilled technicians. An improved reservoir FOCS which is accurate and uniform over a large number of sensors could be the basis of a monitor system.

Another area of application is the continuous sensitive monitoring of certain parameters, particularly oxygen and carbon dioxide in seawater. Dissolved oxygen (DO) is necessary to support all life in the marine environment and is therefore the most important water quality parameter. DO concentration is controlled by a process known as oxygen demand. Oxygen demand materials require oxygen for degradation which results in a depletion of ambient DO levels, thereby depriving marine organisms. Man made wastes, such as sewage sludge and other forms of organic wastes, are examples of oxygen demand materials. These wastes are also known to cause increased nutrient loading resulting in excessive marine plant growth. It is therefore essential to control the amount and type of waste materials dumped into marine waters and to routinely measure and monitor dissolved oxygen to ensure that adequate levels are available to support marine life.

Conditions of low dissolved oxygen often occur in highly populated estuarine and coastal areas. In the summer of 1976, a major oxygen depletion event occurred in the waters off the north eastern coastal United States. Appropriate FOCS technology would be useful for measuring and monitoring changes in oxygen and other biologically important compounds in seawater.

The growing concern over increasing levels of carbon dioxide and other trace gases on a global scale has warranted the need for improved methods for oceanic and atmospheric gas analysis and monitoring. According to recent predictions, "greenhouse" gases in the atmosphere are on a continuous rise and will result in a global warming as much as 2° to 3° C. in the next 50 years.

The ocean flux process permits carbon dioxide to escape from the ocean and depleted oxygen to be replenished. An in-situ measurement capability for dissolved carbon dioxide in the ocean is an important first step toward understanding the ocean flux process. This capability is needed by researchers engaged in ocean and global climate studies. FOCS have the potential to satisfy this need, which was previously unattainable with existing instrumentation.

The need for in situ monitoring of key chemical components in seawater is becoming increasingly more apparent. These components are currently measured by collecting water at the site using specially designed water samplers operated from a manned submersible or from remotely operated vehicles. These samplers are made of titanium, are expensive, and time consuming to clean and maintain. The water samples are then brought to the surface and analyzed by conventional laboratory techniques to determine the results.

There are presently a very limited number of FOCS systems available for commercial use in aqueous systems and virtually none available for use in seawater. Present day methods for the direct measurement of specific chemical parameters in seawater include deployed seawater probes for dissolved oxygen and pH that are based on electrochemistry. These Clark-type probes work either on the galvanic or polarographic principle and have a number of problems including slow response time, reproducibility, chemical and biological fouling of protective membranes, and other effects of high salinity or sensor performance and sensor lifetime. Fiber optic chemical sensors can overcome these problems and will offer many advantages, including batch fabrication at reasonable cost, expendability, small size, light weight and freedom from electromagnetic interference. In FOCS, signals are transmitted optically rather than electrically, which becomes advantageous when handling and deploying long lengths of sea cable in electrically noisy shipboard environments. A reservoir FOCS adapted to these types of measurements will make a groundwater or seawater monitoring system feasible.

SUMMARY OF THE INVENTION

Accordingly, it is an object of the invention to provide an improved reservoir FOCS.

It is also an object of the invention to provide an improved reservoir FOCS which is easy to assemble and which can be reproduced substantially identically in multiple sensors.

It is another object of the invention to provide reservoir FOCS for detecting or measuring TCE vapor, total organic chloride and total organic carbon.

It is a further object of the invention to provide a reservoir FOCS for measuring $O_2$ or $CO_2$ in seawater.

The invention includes a reservoir FOCS formed of a modular reservoir cell body, a precision fiber optic connector which is easily attachable to the cell body for holding an optical fiber precisely positioned within one end of the cell body, a semipermeable membrane, and membrane retainer which is easily attachable to the opposite end of the cell body for holding the membrane in place. The modular cell holds a precise and predetermined amount of liquid reagent and the semipermeable membrane passes the chemical species of interest into the cell to interact with the reagent. The fiber optic receives a signal from the reaction, e.g. fluorescence or absorbance. Optical focusing elements such as Winston cones can be easily positioned within the cell to focus light from the cell volume into the fiber, thereby increasing sensitivity.

The invention also includes a photolysis FOCS system in which a flow through chamber is formed adjacent to a reservoir FOCS with the semipermeable membrane separating the reservoir FOCS from the flow through chamber. The flow chamber has inlet and outlet means for flowing a liquid sample through the chamber and a photolyzing source directed into the chamber. Gaseous photolysis products of chemical species in the liquid sample pass through the semipermeable membrane and are detected in the reservoir FOCS.

DETAILED DESCRIPTION OF THE PREFERRED EMBODIMENTS

Figure 1:
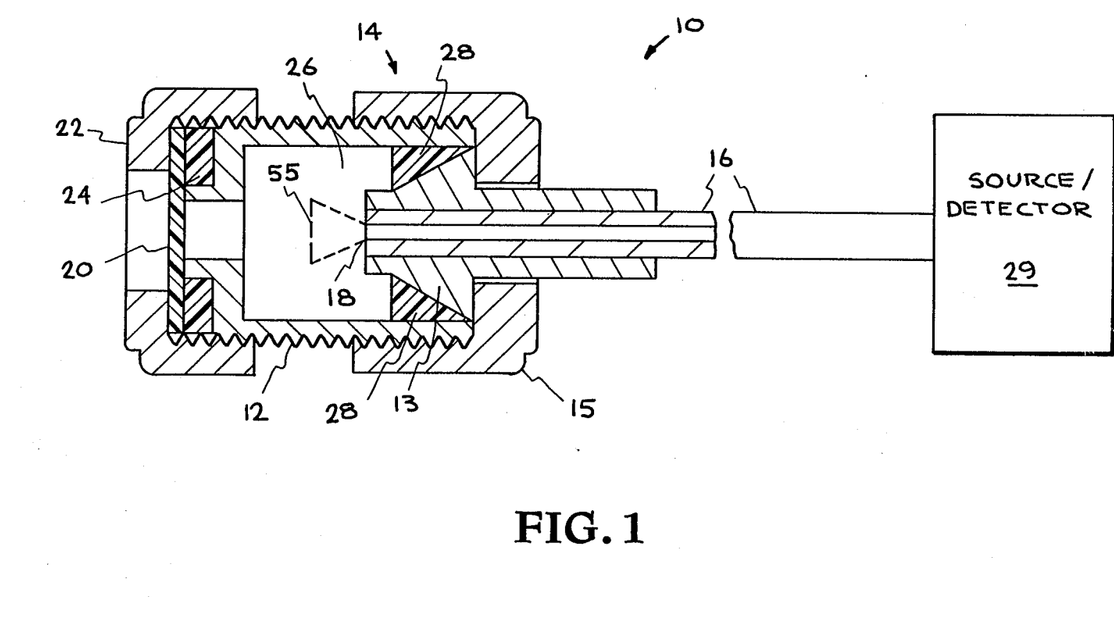
FIG. 1 is a schematic sectional view of a modular reservoir FOCS.

As shown in FIG. 1, a reservoir FOCS 10 is formed of a modular reservoir cell body 12. At one end of cell body 12 is attached a fiber optic connector 14. Fiber optic connector 14 is preferably a standard female fiber optic connector and cell body 12 is threaded to match connector 14 for easy assembly (or disassembly). The connector 14 precisely holds an optical fiber 16 (or fiber bundle) with the fiber optic tip 18 positioned within the cell body 12. Connector 14 is typically made of an inner ferrule 13 in which the fiber optic 16 is held and outer nut or cap 15 which connects to cell body 12. Fiber optic tip 18 may be essentially flush with the end of ferrule 13 to view the cell volume, or a portion of fiber optic 16 may extend beyond the end of ferrule 13 into the cell body. A semipermeable membrane 20 which is held in membrane retainer 22 encloses the cell body 12 by attaching retainer 22 to cell body 12 opposite fiber 16. The retainer 22 also preferably is a female connector which screws onto the threaded modular cell body 12 for easy attachment/disattachment. Membrane 20 is mounted in retainer 22 using a suitable membrane seal 24 such as an O-ring (if necessary) to prevent leakage. The reservoir FOCS, as assembled, encloses a predetermined volume which typically contains a known quantity of liquid reagent 26 within the cell body. The desired chemical species permeate through membrane 20 into cell body 12, interact with reagent 26, and produce an effect, e.g. fluorescence or absorption, which is detected by the fiber optic 16 through the exposed tip 18 positioned in the cell body. A filler polymer 28 may be used to fill the volume around the ferrule 13 to reduce cell volume which fiber tip 18 cannot view. The detection apparatus and light sources required to operate the reservoir FOCS are known in the art and are shown schematically by source/detector assembly 29 which is positioned at the other end of optical fiber 16 from reservoir FOCS 10. The source may be a laser or lamp which provides an excitation or input optical signal to the reservoir FOCS 10 through fiber optic 16. The reservoir FOCS 10 may be a fluorescence cell or absorption cell or any other known type of cell which produces a detectable optical signal which is transmitted back through fiber 16 to assembly 29. Assembly 29 contains a suitable detector as well as a beam splitter and other optics necessary to separate the return signal from the input signal.

Figure 2A:
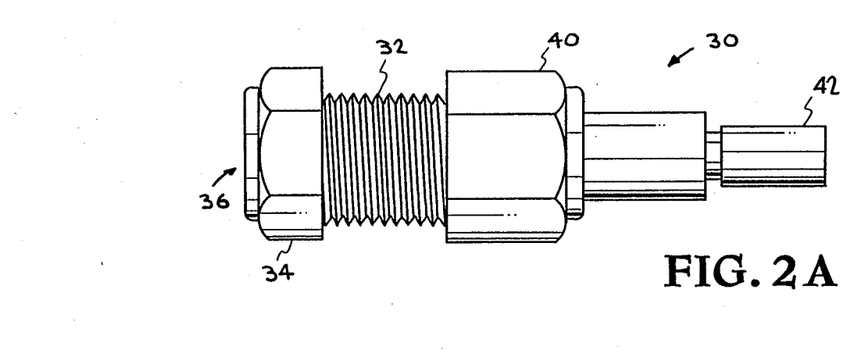
FIGS. 2A,B are perspective views of an assembled and unassembled modular reservoir FOCS, respectively.
Figure 2B:
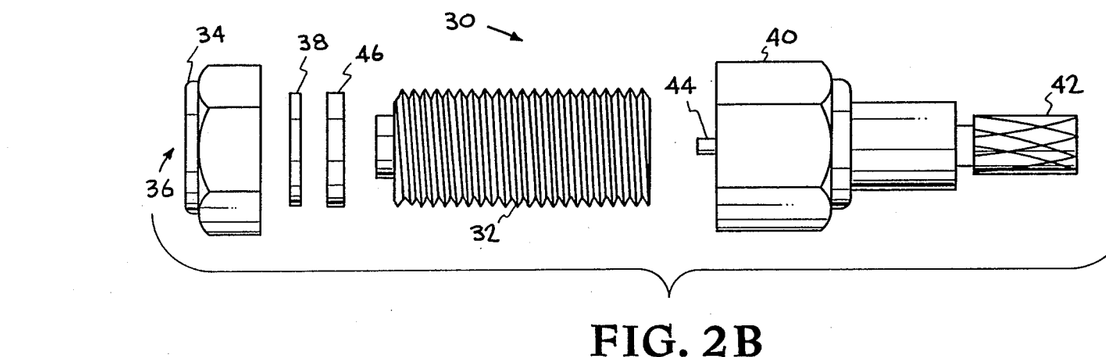

An assembled reservoir FOCS 30 is shown in FIG. 2A. Reservoir FOCS 30 comprises modular cell body 32 which is a threaded cylinder of chosen length and diameter to provide the desired reagent volume. One end of modular cell body 32 is closed by membrane retainer 34 which is a threaded cap which screws onto cell body 32. Retainer 34 has a window 36 formed therein across which a semi-permeable membrane 38 is positioned, with a sealing means 46 formed by a teflon O-ring. When the retainer 34 is connected to cell body 32, membrane 38 is held in place between the cell body 32 and retainer 34. Membrane 38 is selected so that only chemical species of interest can pass through the membrane into the cell body 32. The other end of cell body 32 is closed by a fiber optic connector 40 which also has a threaded cap which screws onto the cell body 32. A sheathed fiber optic cable 42 is connected or attached to connector 40 so that its distal end 44 is positioned within cell body 32. An unassembled view of the reservoir FOCS 30 is shown in FIG. 2B. A number of standard size reservoir cells, e.g. 0.1, 0.5 and 1.0 ml can be produced.

To increase the sensitivity of the reservoir FOCS, an optical focussing element can be positioned in the cell body to focus light into the optical fiber tip. The focussing element can be positioned up against the fiber tip or may be spaced apart from the tip. The optical fiber has a certain numerical aperture, or angle of acceptance for incoming light. Thus the fiber may not be able to detect the entire volume of the reservoir cell. The focussing element allows the fiber to receive signals from a larger volume of the cell and thus improves sensitivity.

Light through-put for chemical sensors attached to fiber-optical communication fibers will be significantly improved by coupling the sensor to the communication fiber through non-imaging optical (NIO) lens couplers. The fluorescence class of sensors requires an NIO coupler with a high numerical aperture, and the absorption cell configuration requires a cell with a very small numerical aperture. Both of these requirements can be met by the NIO lens at a very low unit cost since they can be fabricated from injection molded plastic in large volumes. Additionally, the components for the chemical sensor cell can also be made integral to the NIO lens, greatly improving the reproducibility of the sensor/coupler alignment. These designs can greatly improve the utility of remote optical spectroscopy.

Figure 3:
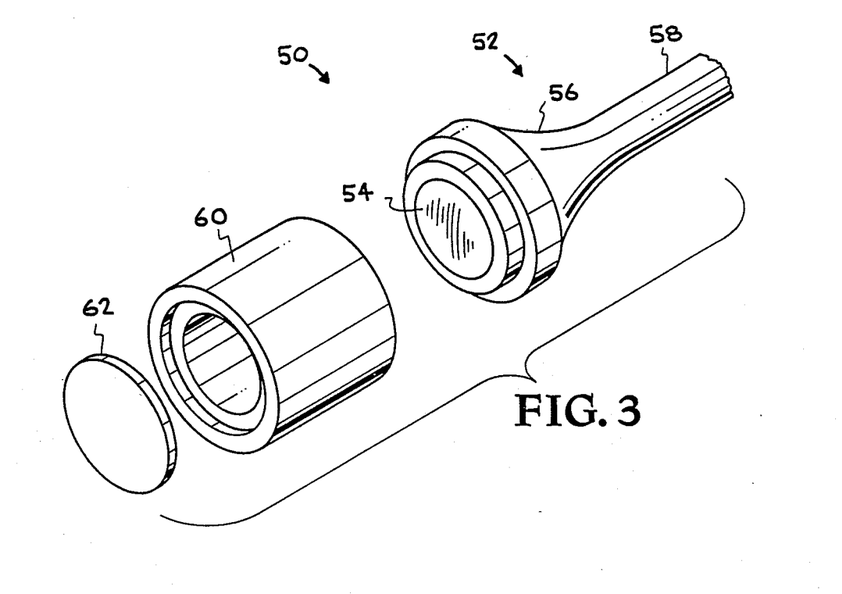
FIG. 3 is a perspective view of a non-imaging optical lens for a reservoir FOCS.

An illustrative example of a reservoir FOCS cell assembly 50 utilizing an integral NIO lens assembly 52 is shown in FIG. 3. NIO lens assembly 52 has a lens 54 held in a lens mount 56 to which an optical fiber 58 is attached. The lens mount 56 fits into one end of modular reagent cell 60 while a membrane 62 is placed across the other end. Mount 56 may simply be pressure fitted into a receptacle in one end of cell 60 or the parts may be threaded so that mount 56 may be screwed into cell 60. Membrane 62 is attached to cell 60 by suitable means. Cell 60 is modular in design having a predetermined size which may be reproduced uniformly.

Alternately, an NIO lens, such as a Winston cone, may be placed in a modular reservoir FOCS sensor of the type shown in FIG. 1, as shown by dotted element 55. The cone can be placed with its apex abutting the fiber optic tip and held in place by suitable means such as simply gluing in place. The cone could also be aligned with but spaced apart from the fiber optic end and held in place by a suitable structure or means.

Thus, an improved optical interface between a chemical sensor and a fiber-optical communication line, may be utilized with or incorporated into a reservoir FOCS. The optical interface comprises a non-imaging optical lens and may be used with both fluorescence sensors and absorption sensors.

In the general class of fluorescence sensors the light which is used to stimulate the fluorescer molecule generally causes photo-degradation or bleaching of that analyte molecule. This limits the intensity of light which may impinge on this molecule for a given sensor lifetime. The limited light intensity, in turn, limits the fluorescence signal which may be generated from a sample of fixed concentration because the fluorescence intensity is proportional to the excitation intensity. It is therefore of utmost importance to collect as much of the fluorescence signal as possible.

The Non-Imaging Optical (NIO) lens is a device which is designed to optimize light through-put for fiber-optical couplers. Its design is optimized for power through-put rather than image quality, as is the case for the classical lens design. When this device with the same numerical output as that of the communication fiber is coupled to the end of a communication fiber and inserted into a chemical sensor a multi-fold increase in the collected fluorescence light is expected from the NIO lens as from an unmodified fiber inserted into the cell at the same light source intensity.

A preferred embodiment of the NIO lens is optimized for communications purposes and has a numerical aperture only one quarter that of the communication fiber, but its performance as a fluorescence coupler is equal to that of the unmodified fiber at 3.4 mm. This design is for a viscous sensor source such that the fluorophor appears to be in a thin disk at approximately 2.5 mm from the emitting end of the NIO lens. The preferred NIO lens device expands the beam radius from 200 $\mu$m to 1 mm. Therefore, for a fixed source intensity, the actual excitation emanating from the NIO lens is only approximately 4% as intense as that form the unmodified fiber source at the surface of the coupler. Thus, the lifetime of the sensor coupled through the NIO lens is expected to be 25 times as long as that using an unmodified fiber at the same lamp power level. Alternatively, the source lamp may be made 25 times as intense, yielding a 25-fold increase in observed signal for two devices of equal output numerical aperture.

For the preferred device the numerical aperture means that the illumination spot-size for the NIO lens increases less rapidly than does that for the unmodified fiber. Thus, where the preferred device shows equal fluorescence power collection, the emitted beam spot-size for the NIO lens is approximately 150% that generated by the unmodified fiber. Therefore, the fluorescence excitation intensity at that point is only approximately 2/3 that from the bare fiber. If the lamp intensity is increased so that the illumination intensity in the NIO coupled system is equal to that of the unmodified fiber at 3.4 mm, a 50% increase in the collected fluorescence signal is expected. These distances are typical for real fluorescence sensors and probes of interest.

A further advantage of the use of the NIO lens in fiber-optic fluorescence sensors and probes is that they more efficiently optically couple the front or far surface of the sensor cells (length less than 5 mm) to the communication fiber due to their greater diameter. The illuminated spot-size is greater than that of the unmodified fiber of equal numerical aperture. More of the analytical material at the front surface will be sampled fluorimetrically giving a faster response time.

Another advantage of the NIO lens as an optical coupler for fluorescence sensors and probes is that they are cast from plastic and that the container for the sensing reagent can be formed integrally with the NIO lens and its holder. This will facilitate replacement of the sensor in an optically reproducible fashion.

The NIO lens concept is also applicable to optical absorption sensors. The use of fiber-optical communication fibers to couple light from a remote sampling facility is hindered by the high dispersion of light emanating from a fiber of even very low numerical aperture. Very little of the light emitted by one fiber may be coupled into an unmodified bare fiber even a millimeter distant. Complicated spherical lens systems to collimate from the emission fiber and refocus the light into the fiber-optical receiver are difficult to fabricate and fragile.

The NIO lens system with its limited numerical aperture is ideal for fabricating an absorbance cell. Because they are fabricated from molded plastic, the cell can be formed of two pieces that can be screwed together and the appropriate flow connections attached. For the NIO lens with a numerical aperture of 0.05 and a radius of 1 mm an optical through-put of 60% is expected with no other optical modifications.

In one particular embodiment, the NIO lens which attaches to a 100 micron fiber and expands the beam to 1.4 mm with a divergence of only 1.4 degrees can be used to form an absorbance cell which is 67% efficient in light collection for a one centimeter cell requiring no additional optics. This one centimeter cell has an internal volume of only 15 microliters.

This type of intrinsic efficiency and small size, coupled with the simplicity of molding the NIO lens with an integral shell which can be threaded so that the two halves of the cell may be screwed together into a rigid system which requires no optical alignment, indicates a wide applicability of the NIO lens. These applications include absorption detection for HPLC where the difficulties of designing detector cells using bulk optics are substantial. Flow cells for flow injection and continuous flow analyzers would be another area of ready application. This application could include small sampling heads for process stream analyzers in production facilities. In each of these areas this cell would allow the optical sampling cell to be placed at some location which is optimized for the analysis rather than at a location which is optimized for bulk optics placement. Thus, connecting flow tubes to the cell can be minimized, in turn, minimizing dead volume and analyte band broadening.

Other applications include areas such as slotted cells which can be dropped into ground waters to quickly monitor absorbance parameters or into biological broths to monitor cell populations. In all of these areas the availability of relatively inexpensive, optically aligned and optimized absorbance cells provides a variety of advantages and new applications for absorbance spectroscopy.

One specific type of reservoir FOCS is an $O_2$ sensor. The $O_2$ FOCS is formed using an oxygen permeable membrane and the reservoir cell is filled with a reagent solution which reacts with oxygen which permeates through the membrane so that when the cell is illuminated by an input or excitation signal through the optical fiber, a measurable output signal is produced.

Luminescence quenching is the basis for the reservoir cell oxygen sensor. Two oxygen sensitive fluorophores, ruthenium tris-bipyridy complex [$Ru^{II}(bpy)_3$] and ruthenium tris-bipyrazyl complex [$Ru^{II}(bpz)_3$], can be used; a reagent solution of either of these can be placed in the reservoir cell. Their structures are as follows:

The tris-bipyridyl complex of ruthenium can be excited between 430 and 490 nm and its emission peak appears at 610 nm. This is an ideal wavelength range to work in. This compound exhibits a very large strokes shift and this makes the "clean" separation of the excitation and emission signals possible. It's first excited triplet energy of 217 kj/mole and triplet lifetime of 670 ns makes it a very interesting choice. Its luminescence is very efficiently quenched by oxygen as evidenced by the high magnitude of the quenching rate constant ($k_q = 3.3 \times 10^9 M^{-1}sec^{-1}$). The second oxygen sensitive fluorophore, the tris-bipyrazyl complex of ruthenium, $Ru(bpz)_3^{2+}$ appears to show even better oxygen response.

For the $O_2$ FOCS, the membrane is not critical because separation of the gas from the liquid (seawater) is not essential for specific, sensitive analyses; i.e. the sensor will respond to $O_2$ which permeates into the cell even if some of the sample solution also enters the cell. Nafion polymer is one possible membrane material.

Another specific type of reservoir FOCS is a $CO_2$ sensor. Since the dissolution of $CO_2$ in water alters the pH of the medium, a pH sensitive dye in aqueous solution is used as the sensing reagent in a $CO_2$ reservoir cell FOCS.

The detection of $CO_2$ is accomplished by taking advantage of the equilibrium;

$$CO_2 + H_2O \longleftrightarrow H_2CO_3 \longleftrightarrow H^+ + CO_3^-$$

In this system the concentration of $H_2CO_3$ is directly related to the amount of $CO_2$ present. In sea water $CO_2$ is the only gas present capable of forming an acid with the water and thus a pH measurement can be a direct measurement of the $CO_2$ concentration.

In practice the pH FOCS chemistry is separated from the sea water by a gas permeable, liquid impermeable membrane. Thus no liquid reaches the sensing reagents and the pH measured is for the $H_2CO_3$ only!

The key to good $CO_2$ sensitivity is to choose either a fluorophore or energy exchange system whose pKa is close to that of $H_2CO_3$ at the concentrations expected (pKa—7.2). HPTS (hydroxypyrenetrisulfonate) is a preferred pH sensitive fluorophore for the detection of $CO_2$. It is water soluble (before immobilization), has good stability (better than fluorescein) and has a pKa of 7.3 which is close to the $H_2O + CO_2 \longleftrightarrow H_2CO_3$ equilibrium at the anticipated $CO_2$ concentrations. In addition, the compounds listed in Table III below are other pH sensitive reagents which may be used in a pH FOCS, for either direct fluorescence or absorption measurements at the indicated pH ranges.

Figure 4:
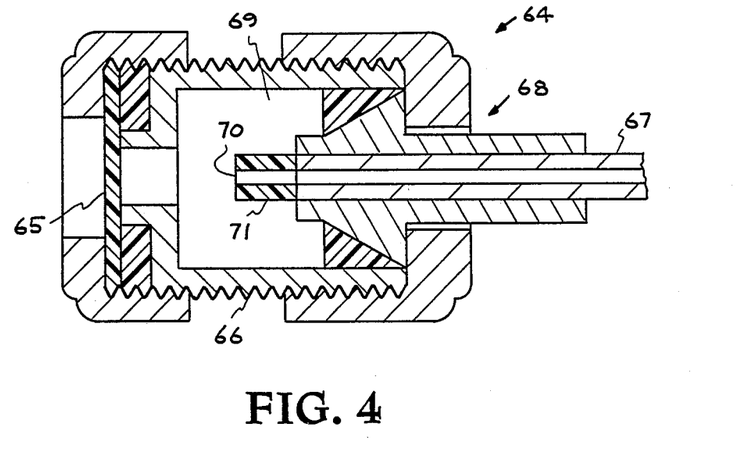
FIG. 4 is a schematic view of a TCE vapor reservoir FOCS.

A reservoir FOCS for TCE vapor will be in many ways similar to the one shown in FIGS. 1, and 2A,B. The sensor 64, as shown in FIG. 4, has a gas permeable membrane 65 at one end of cell body 66 while the other end contains the fiber optic 67 held in connector 68. For TCE teflon membranes can be used. The cell would be completely sealed so that mass diffusion of the vapors can only occur through the membrane. When the probe is immersed in water the TCE vapor would diffuse into the measurement volume 69 of the FOCS. The cell volume 69 would be empty rather than filled with a liquid reagent. The detection of TCE would then be done by refractive index-matching. The end 70 of the fiber (core) would extend into reservoir and the side would be coated with a specific reaction chemistry 71 that reacts with TCE to change light transmission of the fiber. This sensor would be completely reversible and the amount of volatiles entering, or exiting, through the membrane would depend on their vapor pressure in the water sample.

The simplest detection and quantification scheme for TOCl would be a process which would convert the covalently bound halogen atoms into elementary halogen or halide anions. Then the analysis would be a rudimentary measurement of inorganic chloride or chlorine.

Decomposition of the organic chlorides cannot be accomplished by any single chemical method (i.e. oxidation, reduction, etc.). Thus the chemical route for decomposition is specific to a particular organic chloride. In addition, for rapid, reliable, reproducible analysis none of the available chemical approaches appear suitable for fiber optic adaptation. The most practical solution, therefore, is to photolyze the organic chlorides to yield $Cl_2$. This can be accomplished with ultraviolet light which causes the C-halogen bond to break and the formation of $Cl_2$.

The ease of bond homolysis depends on the strength of the bond to be broken. Table I shows the C-halogen bond strengths of some common organic halides. $CH_4$ represents the strongest bond of the aliphatic organic hydrocarbons.

TABLE I
CARBON - HALOGEN BOND STRENGTHS

| BOND TYPE | SAMPLE COMPOUND | BOND STRENGTH (kJ mole$^{-1}$) |
|---|---|---|
| C—Cl | $CH_3Cl$ | 326 |
|  | $H_2C=CHCH_2Cl$ | 251 |
| C—Br | $CH_3Br$ | 280 |
|  | $C_6H_5Br$ | 297 |
| C—I | $CH_3I$ | 213 |
|  | $H_2C=CHCH_2I$ | 142 |
| C—H | $CH_4$ | 414 |

Light in the ultraviolet region has energy in excess of the bond dissociation energies of the alkyl halides. For example, light at a wavelength of 254 nm (available from a low pressure mercury lamp) is equivalent to 470 kJ/einstein. Light absorption in the C-halogen bond occurs, principally, by means of a n→σ* transition. After the absorption of photons, dissociation of the C-halogen bond occurs in a homolytic fashion. A common sequence of reactions is:

$RX + h\nu \rightarrow R^* + X^*$ $R^* + X^* \rightarrow RX$ $R^* + R^* \rightarrow R\text{—}R$ $X^* + X^* \rightarrow X_2$ The last step would lead to the selective formation of halogen during the photolysis.

Figure 5:
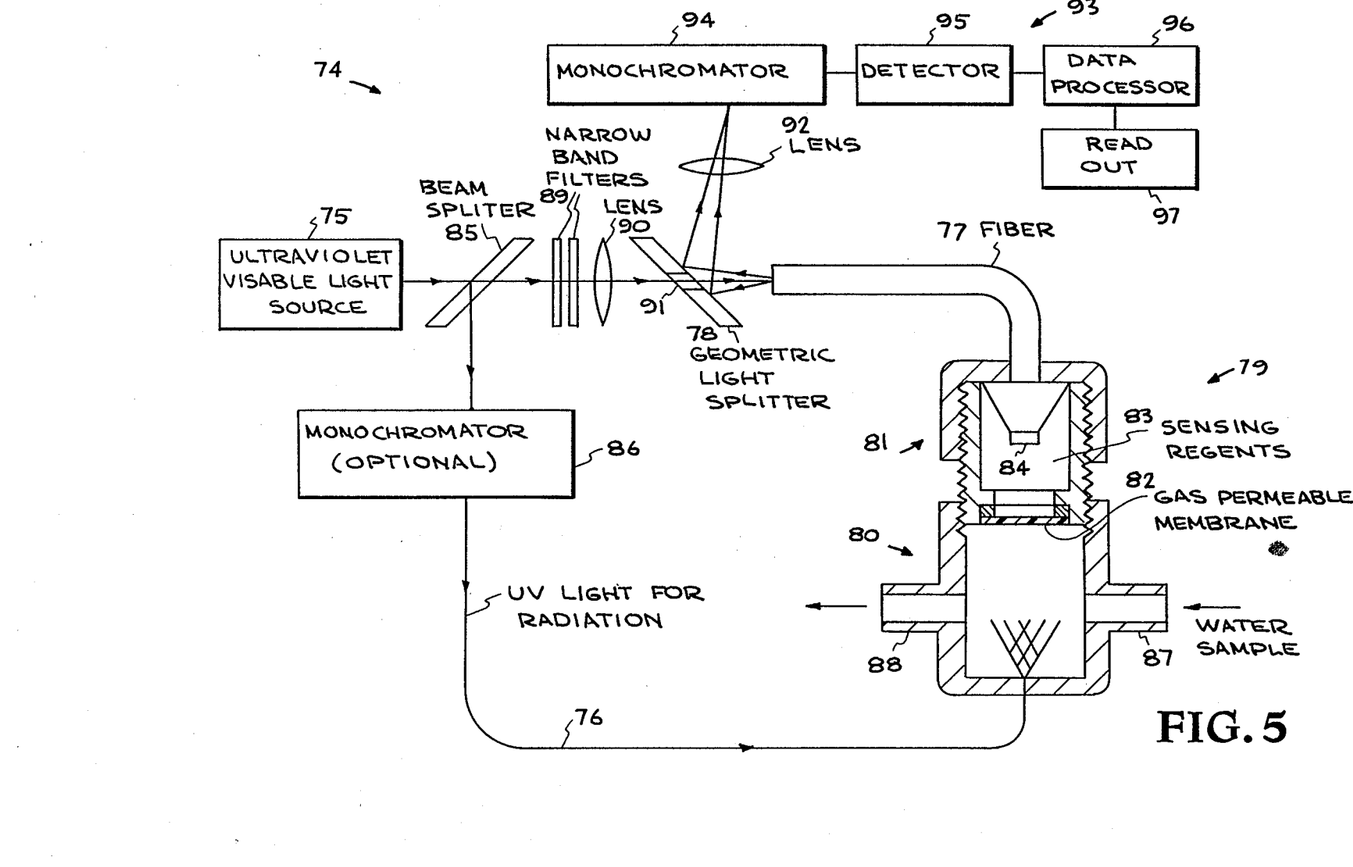
FIG. 5 is a schematic view of a photolysis FOCS system.

FIG. 5 is a schematic of the TOCl FOCS system 74. A mercury lamp or other UV/visible light source 75 is used both to provide the ultraviolet light necessary to photolyze the organic halides and to excite the sensing reagents. Alternately, two separate light sources could be used. Quartz fiber optics are used to transmit the ultraviolet light. One fiber 76 is used to transmit the light for photolysis and a second fiber 77 (with a geometric splitter 78) is employed to both excite the sensing reagent(s) and to send the return signal to a spectral sorter. The FOCS 79 includes a reaction cell 80 which can be operated in a continuous flow through or static (closed) mode. The sensor 79 has two sections separated by a gas permeable membrane 82. One section is the reaction (conversion) cell 80 and the other section is a reservoir cell 81 as previously described (but designed for chlorine or halogens) where the actual chemical analysis occurs. The volatile chloride (or halogens), which is evolved during the photolysis, will diffuse through the gas permeable membrane 82 and react with an appropriate sensing material (reagent) 83. The distal end 84 of the fiber 77 is placed inside the sensing solution and color changes are monitored as it reacts with various $Cl_2$ concentrations.

Light from source 75 is incident onto beam splitter 85 which splits the beam into two parts. One part passes through (optional) monochromator 86 (if necessary) to select the desired UV wavelength to photolize the chloride (halogen) and then is transmitted through fiber optic 76 to reaction cell 80. Fiber optic 76 extends into reaction cell 80, e.g. in a manner similar to that of the reservoir cell so that UV light is emitted from the fiber 76 into the interior volume of reaction cell 80. Sample may be flowed through reaction cell 80 by inlet and outlet ports 87,88 or a nonflowing sample may be used. Light from fiber 76 photolyzes any chloride in the sample and the $Cl_2$ produced permeates across membrane 82 and reacts with sensing reagent 83. The other part of the beam from source 75 passes through beam splitter 85, narrow band filters 89, lens 90 and small aperture 91 in light splitter 78 into one end of fiber 77. The light is transmitted by fiber 77 to reservoir cell 81 and exits end 84 into sensing reagent 83. A return signal produced by the reaction of $Cl_2$ with reagent 83 passes through tip 84 and through fiber 77 back to light splitter 78. Since the return signal is diverging instead of highly focused like the input beam, little of the light passes back through aperture 91 and most is reflected through lens 92 to the detection system 93 which is made up of monochromator 94, detector 95, data processor 96 and read out 97.

The photolysis sensor can be made of a modular design similar to the reservoir cell. It is formed of a reservoir cell with a second cell (the reaction or conversion cell) connected thereto with the semipermeable membrane separating the two cells.

In selecting the proper sensing reagent to detect an environmental target compound, or class of compounds, it is necessary to address five (5) concerns: (i) choose a reaction that specifically detects and quantifies the species of interest, (ii) determine if this chemistry is amenable for use with a fiber optic, (iii) assess whether a practical measurement technique exists, (iv) evaluate whether other compounds present in the background matrix may interfere with the analysis and (v) ascertain whether the FOCS will be fouled by other materials present.

For the detection of free halogen, and principally $Cl_2$, sensing reagents will be chosen so that sharp, dramatic color changes are observed after the reaction. In selecting these sensing reactions, compounds specific to $Cl_2$ and other free halogen can be used. In most contaminated systems organic chlorides are present in much higher concentrations than the other organic halides. Sensing reagents which respond to $Br_2$ and $I_2$ as well as $Cl_2$ may, therefore, be acceptable because in "real life" situations there would not be much of these other halogens present. Only chlorine would preferentially react with these reagents facilitating the measurement of total organic chloride. Table II shows a list of reagents which are sensitive to halogens.

TABLE II
COLOR REACTIONS FOR FREE HALOGEN*

| Reagent | Color Reaction |
|---|---|
| Diphenylamine | Colorless to Blue |
| Thio-Michler's Ketone | Brown-Yellow to Blue |
| N,N—Dimethyl-p-phenylene diamine | Colorless to Red |
| Iodine - Starch | Colorless to Blue |
| Congo Red - $H_2O_2$* | Red to Blue |
| O—tolidine* | Colorless to Yellow |

*$Cl_2$ specific reagents

A similar method and apparatus are used to detect TOC. Ultraviolet photolysis of organic compounds leads to the formation of $CO_2$. The same approach, therefore, will be used to set up a detection scheme for TOC similar to that for TOCl. In this case, however, the sensing reagent(s) in the detection part of the FOCS would be sensitive to $CO_2$ only. The energy of the ultraviolet light is more than sufficient to rupture the C—C bond. The dissolved $O_2$ in water would be used to oxidize organic carbon to $CO_2$. A photolysis reservoir FOCS similar to that for TOCl and as shown schematically in FIG. 5 can thus be used to detect and measure TOC. The reservoir cell portion of the TOC FOCS is just a CO₂ reservoir FOCS.

A preferred sensing material for $CO_2$ monitoring is hydroxypyrenetrisulfonic acid (HPTS) trisodium salt. HPTS is a reversible pH sensitive dye. When $CO_2$ dissolves in water, the hydrogen ion concentration in unbuffered water is increased, as indicated by the following reactions.

$$CO_2 + H_2O \longleftrightarrow H_2CO_3 \longleftrightarrow H^+ + CO_3^-$$

The presence of $CO_2$, therefore, changes the pH of the solution depending on its concentration. As with the TOCl system the photolysis side of the FOCS is separated from the analytical part by a gas permeable membrane. This membrane excludes protons (which affect pH) but allows the $CO_2$ to enter the sensing region. Since only the $CO_2$ can change the pH of the analytical system, under these conditions, pH is a direct measure of $CO_2$ concentration. The pH is determined by measuring intensity changes in the HPTS fluorescence.

Table III shows other pH sensitive reagents which might be used, in either a fluorescence or absorption type detector system.

TABLE III

| pH Range | Direct Fluorescence | Energy Exchange With Eosin |
|---|---|---|
| 2.4 to 4.0 | | 2,6 Dinitrophenol |
| 3.1 to 4.4 | Morin | |
| 4.0 to 5.8 | | 25 Dinitrophenol |
| 5.2 to 6.6 | Acridine | |
| 5.6 to 7.2 | | Dibromophenoltetrabromo-phenolsulfonthalien |
| 6.0 to 7.0 | Luminol | |
| 6.0 to 8.0 | | Curcumin |
| 6.5 to 8.0 | Orcinourine | |
| 7.2 to 8.8 | | Cresol Red |
| 7.4 to 9.0 | | Metacresol Purple |

Changes and modifications in the specifically described embodiments can be carried out without departing from the scope of the invention which is intended to be limited only by the scope of the appended claims.

We claim:

1. A reservoir cell assembly for a fiber optic chemical sensor, comprising:
   a modular cell body having a predetermined length and enclosing a predetermined volume and having two open ends;
   a semipermeable membrane positioned at one open end of the cell body;
   quick attach membrane retainer means which fit securely to one open end of the cell body to hold the membrane in place so that a predetermined chemical species may selectively diffuse through the membrane into the cell;
   quick attach fiber optic connector means which fit securely to the other end of the cell body to hold the fiber optic positioned with its tip extending through the connector means into the cell body.

2. The cell assembly of claim 1 wherein the modular cell body comprises a substantially tubular body with threads on its outer surface for attachment of the fiber optic connection means and membrane retainer means.

3. The cell assembly of claim 2 wherein the fiber optic connection means is a standard fiber optic connector comprising an inner ferrule or an outer cap.

4. The cell assembly of claim 1 further comprising a sensing reagent solution which fills the reservoir cell body and is reactive with the predetermined chemical species.

5. The cell assembly of claim 1 further comprising an optical fiber having a distal end mounted in the fiber optic connection means.

6. The cell assembly of claim 5 further comprising source and detector means operatively coupled to the other end of the optical fiber for inputting an optical signal into the cell body through the optical fiber and detecting an optical signal from the cell body through the optical fiber.

7. The cell assembly of claim 1 further comprising a non-imaging optical focusing element positioned in the cell body and optically aligned with the tip of the fiber optic.

8. The cell assembly of claim 7 wherein the non-imaging optical focusing element is a Winston cone.

9. The cell assembly of claim 7 wherein the cell is a fluorescence cell and the non-imaging optical focusing element has a high numerical aperture.

10. The cell assembly of claim 7 wherein the cell is an absorption cell and the non-imaging optical focusing element has a low numerical aperture.

11. The cell assembly of claim 7 wherein the non-imaging optical focusing element is an injection molded plastic lens formed integrally with the fiber optic connector and attached to an optical fiber.

12. The cell assembly of claim 5 wherein the end of the optical fiber extends into the cell body from the fiber optic connector means and further comprises a fiber optic core coated with a reaction chemistry specific to the predetermined chemical species.

13. The cell assembly of claim 12 wherein the membrane is permeable to TCE vapor and the fiber optic core extending into the cell body is coated with a reaction chemistry which reacts with TCE to alter light transmission by the fiber.

14. The cell assembly of claim 4 wherein the membrane is permeable to oxygen and the reagent solution is selected from $Ru(bpy)_3^{2+}$ and $Ru(bpz)_3^{2+}$ solutions.

15. The cell assembly of claim 4 wherein the membrane is permeable to carbon dioxide and the reagent solution is a pH sensitive dye solution.

16. The cell assembly of claim 15 wherein the dye solution is a hydroxypyrenetrisulfonate solution.

17. The cell assembly of claim 1 further comprising a reaction cell mounted adjacent to the reservoir cell body with the membrane separating the reaction cell from the reservoir cell body.

18. The cell assembly of claim 17 further comprising a light source operatively connected to the reaction cell to photolyze a predetermined compound in a sample within the reaction cell, and a reagent solution in the adjacent reservoir cell body which is reactive with photolysis products produced in the reaction cell, and wherein the membrane is permeable to the photolysis products.

19. The cell assembly of claim 18 further comprising detector means operative connected to the reservoir cell body for detecting the reaction of the photolysis products with the reagent solution in the cell body.

20. A photolysis fiber optic chemical sensor apparatus, comprising:
   a sensor assembly comprising:
      a reservoir cell filled with a reagent solution reactive with predetermined photolysis products;
      a reaction cell adjacent to the reservoir cell;

a semipermeable membrane separating the reservoir cell from the reaction cell, which is permeable to the predetermined photolysis products;

a light source which produces light of a predetermined wavelength;

means for transmitting light of the predetermined wavelength into the reaction cell to photolyze a predetermined species in a sample placed in the reaction to produce the predetermined photolysis products;

means for detecting reaction of the predetermined photolysis products with the reagent solution in the reservoir cell.

* * * * *